United States Patent [19]

Nishiyama et al.

[11] 4,173,638
[45] * Nov. 6, 1979

[54] N-BENZOYL-N'-PYRIDYLOXY PHENYL UREA AND INSECTICIDAL COMPOSITIONS THEREOF

[75] Inventors: Ryuzo Nishiyama, Takatsuki; Kanichi Fujikawa, Kyoto; Rikuo Nasu, Kusatsu; Tadaaki Toki, Kusatsu; Toshihiko Yamamoto, Kusatsu, all of Japan

[73] Assignee: Ishihara Sangyo Kaisha Ltd., Osaka, Japan

[ * ] Notice: The portion of the term of this patent subsequent to Nov. 6, 1996, has been disclaimed.

[21] Appl. No.: 844,174

[22] Filed: Oct. 21, 1977

[30] Foreign Application Priority Data

Oct. 29, 1976 [JP] Japan ................................. 51/130903

[51] Int. Cl.² ..................... A61K 31/44; C07D 213/64
[52] U.S. Cl. .................................. 424/263; 546/297; 546/300
[58] Field of Search ..................... 260/295 E; 424/263; 546/297, 300

[56] References Cited

U.S. PATENT DOCUMENTS 3,748,356  7/1973  Wellinga et al. ................. 260/295 E
4,005,223  1/1977  Sirrenberg et al. ................. 424/322

OTHER PUBLICATIONS

March, J., Advanced Organic Chemistry, McGraw-Hill, New York, 1968, pp. 672–673.

Primary Examiner—John M. Ford
Assistant Examiner—Richard A. Schwartz
Attorney, Agent, or Firm—Oblon, Fisher, Spivak, McClelland & Maier

[57] ABSTRACT

N-benzoyl N'-pyridyloxy phenyl urea having the formula

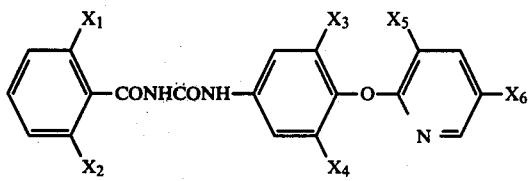

wherein $X_1$ represents a halogen atom; $X_2$ represents hydrogen or halogen atom; $X_3$ and $X_4$ respectively represent hydrogen or chlorine atom; $X_5$ represents hydrogen or halogen atom; and $X_6$ represents a halogen atom or nitro or trifluoromethyl group are novel compounds.

The compositions containing the compound as the active ingredient are effective as the insecticide for extinction of injurious insects with high safety in agricultural, forestry and hygienic applications.

17 Claims, No Drawings

N-BENZOYL-N'-PYRIDYLOXY PHENYL UREA AND INSECTICIDAL COMPOSITIONS THEREOF

BACKGROUND OF THE INVENTION

1. Field of the Invention

The present invention relates to novel N-benzoyl N'-pyridyloxy phenyl ureas and the process for producing the same and the insecticidal composition containing the same.

2. Description of the Prior Arts

Almost of the conventional insecticides impart neurotoxicity and contact toxicity to all kinds of insects.

And, it has been required to find selective insecticidal compounds without toxicity to useful insects, N-benzoyl N'-phenyl ureas disclosed in U.S. Pat. No. 3,748,356 have such insecticidal properties.

The N-benzoyl N'-pyridyloxyphenyl ureas according to the present invention have a substantially better action than the above described known compounds.

SUMMARY OF THE INVENTION

It is an object of the present invention to provide novel N-benzoyl N'-pyridyloxy phenyl ureas.

It is another object of the present invention to provide a process for producing N-benzoyl N'-pyridyloxy phenyl ureas.

It is the other objects of the present invention to provide selective insecticidal compositions which are remarkably effective to certain injurious insects without affecting useful insects in remarkably low toxicity to animals.

The novel compounds of the present invention are N-benzoyl N'-pyridyloxy phenyl ureas having the formula

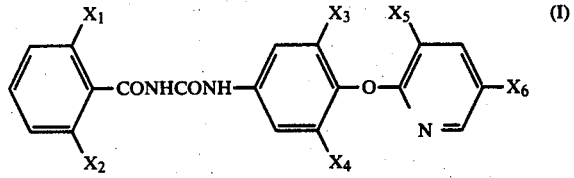

wherein $X_1$ represents a halogen atom; $X_2$ represents hydrogen or halogen atom; $X_3$ and $X_4$ respectively represent hydrogen or chlorine atom; $X_5$ represents hydrogen or halogen atom; and $X_6$ represents a halogen atom or nitro or trifluoromethyl group.

DESCRIPTION OF THE PREFERRED EMBODIMENTS

Suitable compounds having the formula (I) include:
N-(2-chlorobenzoyl)N'-[3-chloro-4-(5-bromopyridyl-2-oxy) phenyl]urea m.p. 196° to 199° C.
N-(2-chlorobenzoyl)N'-[3-chloro-4-(5-nitropyridyl-2-oxy) phenyl]urea m.p. 209° to 212° C.
N-(2-chlorobenzoyl)N'-[4-(3,5-dibromopyridyl-2-oxy) phenyl]urea m.p. 185° to 188° C.
N-(2-chlorobenzoyl)N'-[3-chloro-4-(3,5-dibromopyridyl-2-oxy) phenyl]urea m.p. 223° to 224° C.
N-(2-chlorobenzoyl)N'-[4-(3,5-dichloropyridyl-2-oxy) phenyl]urea m.p. 216° to 218° C.
N-(2-chlorobenzoyl)N'-[3-chloro-4-(3,5-dichloropyridyl-2-oxy) phenyl]urea m.p. 225° to 228° C.
N-(2-chlorobenzoyl)N'-[3,5-dichloro-4-(3,5-dichloropyridyl-2-oxy) phenyl]urea m.p. 221° to 223° C.
N-(2-chlorobenzoyl)N'-[4-(5-bromopyridyl-2-oxy) phenyl]urea m.p. 179° to 180° C.
N-(2-chlorobenzoyl)N'-[3-chloro-4-(5-chloropyridyl-2-oxy) phenyl]urea m.p. 198° to 200° C.
N-(2-chlorobenzoyl)N'-[3,5-dichloro-4-(5-chloropyridyl-2-oxy) phenyl]urea m.p. 147° to 148° C.
N-(2-chlorobenzoyl)N'-[4-(5-trifluoromethylpyridyl-2-oxy) phenyl]urea
N-(2-chlorobenzoyl)N'-[3-chloro-4-(5-trifluoromethylpyridyl-2-oxy) phenyl]urea
N-(2,6-dichlorobenzoyl)N'-[4-(3,5-dichloropyridyl-2-oxy) phenyl]urea m.p. 228° to 230° C.
N-(2,6-dichlorobenzoyl)N'-[3-chloro-4-(3,5-dichloropyridyl-2-oxy) phenyl]urea m.p. 214° to 216° C.
N-(2,6-dichlorobenzoyl)N'-[3,5-dichloro-4-(3,5-dichloropyridyl-2-oxy) phenyl]urea m.p. 273° to 275° C.
N-(2,6-difluorobenzoyl)N'-[4-(3,5-dichloropyridyl-2-oxy) phenyl]urea m.p. 184° to 185° C.
N-(2,6-difluorobenzoyl)N'-[3-chloro-4-(3,5-dichloropyridyl-2-oxy) phenyl]urea m.p. 230° to 231° C.
N-(2,6-difluorobenzoyl)N'-[3-chloro-4-(5-chloropyridyl-2-oxy) phenyl]urea m.p. 210° to 212° C.

The N-benzoyl N'-pyridyloxy phenyl ureas having the formula (I) are produced by reacting a compound having the formula

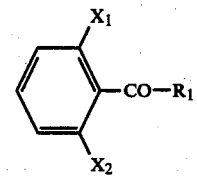

wherein $X_1$ represents a halogen atom; $X_2$ represents hydrogen or halogen atom; $R_1$ represents amino or isocyanate group with a compound having the formula

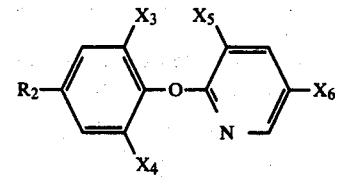

wherein $X_3$ and $X_4$ are the same and different and respectively represent hydrogen or chlorine atom; $X_5$ represents hydrogen or halogen atom; $X_6$ represents halogen atom or nitro or trifluoromethyl group; and $R_2$ represents an amino or isocyanate group and $R_2$ is amino group in the case that $R_1$ is isocyanate group, $R_2$ is isocyanate group in the case that $R_1$ is amino group.

More particularly, the compounds having the formula (I) can be produced by the following processes (1) and (2).

(1) The reaction of benzoyl isocyanate having the formula

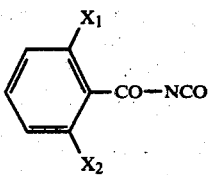

with pyridyloxy aniline having the formula

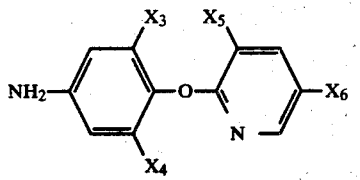

(wherein $X_1$, $X_2$, $X_3$, $X_4$, $X_5$ and $X_6$ are defined above) (2) The reaction of benzamide having the formula

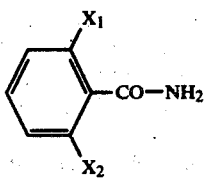

with pyridyloxy phenyl isocyanate having the formula

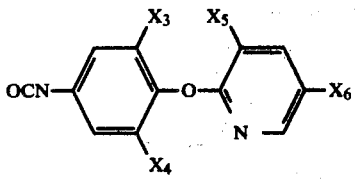

(wherein $X_1$, $X_2$, $X_3$, $X_4$, $X_5$, and $X_6$ are defined above).

The reaction is preferably carried out in the presence of a solvent. Suitable solvents include benzene, toluene, xylene, pyridine etc.

The reaction temperature is usually in a range of 20° to 120° C. and the reaction time is usually in a range of 0.5 to 24 hours. The reaction is preferably carried out at the temperature from 50° C. to a refluxing temperature for 1 to 5 hours.

Certain examples of preparations of the compounds of the present invention will be described.

EXAMPLE 1

Preparation of N-(2-chlorobenzoyl)N'-[3-chloro-4-(3,5-dichloropyridyl-2-oxy) phenyl]urea A solution prepared by dissolving 2.9 g of 3-chloro-4-(3,5-dichloro-pyridyl-2-oxy) aniline in 50 ml of toluene was heated at 80° C. A solution prepared by dissolving 1.8 g of 2-chlorobenzoyl isocyanate in 20 ml of toluene was added dropwise to the former solution under stirring it and the reaction was carried out for 1 hour. After the reaction, the reaction mixture was cooled and the precipitate was filtered and washed with toluene and then with petroleum ether and dried to obtain 3.2 g of N-(2-chlorobenzoyl)N'-[3-chloro-4-(3,5-dichloropyridyl-2-oxy)phenyl]urea (m.p. 225° to 228° C.).

EXAMPLE 2

Preparation of N-(2,6-dichlorobenzoyl)N'-[4-(3,5-dichloropyridyl-2-oxy) phenyl]urea In accordance with the process of Example 1, except using 2.5 g of 4-(3,5-dichloropyridyl-2-oxy) aniline instead of 3-chloro-4-(3,5-dichloropyridyl-2-oxy) aniline and using 2.4 g of 2,6-dichlorobenzoyl isocyanate instead of 2-chlorobenzoyl isocyanate and reacting at 30° C. for 8 hours instead of 80° C. for 1 hour, the process was repeated to obtain 3.8 g of N-(2,6-dichlorobenzoyl)N'-[4-(3,5-dichloropyridyl-2-oxy) phenyl]urea (m.p. 228° to 230° C.).

The compounds of the present invention impart excellent selective insecticidal effect as clearly understood from the following experiments.

Most of the conventional insecticides impart quick effect and neurotoxicity and contact toxicity. However, the compounds of the present invention impart the delayed effect that the compounds effect to molting (ecdysis) and metamorphosis of specific insects which orally take the compound with feeds or water whereby the death of the specific insects is caused.

The compounds of the present invention impart remarkable insecticidal effect to larvae of Lepidoptera, Coleoptera, Hymenoptera and Diptera, for example, larvae of the following insects:

diamondback moth (*Plutella xylostella*), common white (*Pieris rapae crucivora*), cabbage armyworm (*Mamesta brassicae*), cabbage looper (*Plusia nigrisigma*), tobacco cutworm (*Prodenia litura*), smoller citrus dog (*Papilio xuthus*), small blackfish cochlid (*Seopelodes contracta*), fall webworm (*Hyphantria cunea*), gypsy moth (*Lymantria dispar*), rice stem borer (*Chilo suppressalis*), bollworm (*Heliothis zea*), tobacco budworm (*Heliothis virescens*), bollweevil (*Anthonomus grandis*), confused flour beetle (*Tribolium confusum*), colorado potato beetle (*Leptinotarsa decemlineata*), sawfly (*Neurotoma irdescens*), Culex mosquito (*Culex pipiens pallens*).

The compounds of the present invention do not substantially impart insecticidal effect to adults and are ineffective to natural enemies as predatory insects and impart low toxicity to animals.

When the compounds are used as active ingredients of the insecticidal composition, it is possible to prepare various forms of the compositions such as dust, wettable powder, emulsifiable concentrate, invert emulsion, oil solution, aerosol preparation, etc. with adjuvants as the cases of agricultural compositions. The compositions can be applied with or without diluting them in suitable concentrations.

Suitable adjuvants include powdery carriers such as talc, kaolin, bentonite, diatomaceous earth, silicon dioxide, clay and starch; liquid diluents such as water, xylene, toluene, dimethylsulfoxide, dimethyl formamide, acetonitrile, and alcohol; emulsifiers dispersing agents spreaders etc.

The concentration of the active ingredient in the selective insecticidal composition is usually 5 to 80 wt.% in the case of the oily concentrate; and 0.5 to 30 wt.% in the case of dust; 5 to 60 wt.% in the case of wettable powder.

It is also possible to combine with the other agricultural ingredients such as the other insecticides, miticides, plant growth regulators. Sometimes synergetic effects are found.

The selective insecticides of the present invention are effective for inhibiting various injurious insects and they are usually applied at a concentration of the active ingredients of 5 to 10,000 ppm preferably 20 to 2,000 ppm.

EXPERIMENT 1

The active ingredients were respectively dispersed in water to prepare dispersions having specified concentrations. Leaves of cabbage were dipped into the dispersions for about 10 seconds and taken out and dried under passing air.

A piece of moistened filter paper was put on each Petri dish (diameter 9 cm) and the dried leaves of cabbage were put on the filter paper and larvae of diamondback moth in 2nd or 3rd instar were fed on them and the Petri dishes were covered and kept in constant temperature at 28° C. with lightening. After 8 days from the treatment with the dispersion, the dead larvae were measured and the mortality rates were calculated by the following equation:

$$\text{Mortality rate} = \frac{\text{Dead larvae}}{\text{total larvae}} \times 100$$

Table 1

| No. | Active ingredient | Mortality Rate (%) (concentration) 200 ppm | 100 ppm |
|---|---|---|---|
| 1 | N-(2-chlorobenzoyl)N'-[3-chloro-4(5-bromo-pyridyl-2-oxy)phenyl]urea | 100 | 100 |
| 2 | N-(2-chlorobenzoyl)N'-[3-chloro-4-(5-nitro-pyridyl-2-oxy)phenyl]urea | 100 | 100 |
| 3 | N-(2-chlorobenzoyl)N'-[4-(3,5-dibromo-pyridyl-2-oxy)phenyl]urea | 100 | 100 |
| 4 | N-(2-chlorobenzoyl)N'-[3-chloro-4-(3,5-dibromopyridyl-2-oxy)phenyl]urea | 100 | 100 |
| 5 | N-(2-chlorobenzoyl)N'-[4-(3,5-dichloro-pyridyl-2-oxy)phenyl]urea | 100 | 100 |
| 6 | N-(2-chlorobenzoyl)N'-[3-chloro-4-(3,5-dichloropyridyl-2-oxy)phenyl]urea | 100 | 100 |
| 7 | N-(2,6-dichlorobenzoyl)N-[4-(3,5-dichloropyridyl-2-oxy)phenyl]urea | 100 | 100 |
| 8 | N-(2,6-dichlorobenzoyl)N'-[3-chloro-4-(3,5-dichloropyridyl-2-oxy)phenyl]urea | 100 | 100 |
| 9 | N-(2-chlorobenzoyl)N'-[3,5-dichloro-4-(3,5-dichloropyridyl-2-oxy)phenyl]urea | 100 | 80 |
| 10 | N-(2,6-dichlorobenzoyl)N'-[3,5-dichloro-4-(3,5-dichloropyridyl-2-oxy)phenyl]urea | 80 | 60 |
| 11 | N-(2,6-difluorobenzoyl)N'-[4-(3,5-dichloropyridyl-2-oxy)phenyl]urea | 100 | |
| 12 | N-(2,6-difluorobenzoyl)N'-[3-chloro-4-(3,5-dichloropyridyl-2-oxy)phenyl]urea | 100 | 100 |
| 13 | N-(2-chlorobenzoyl)N'-[4-(5-bromo-pyridyl-2-oxy)phenyl]urea | 100 | 100 |
| 14 | N-(2-chlorobenzoyl)N'-[3-chloro-4-(5-chloropyridyl-2-oxy)phenyl]urea | 100 | 100 |
| 15 | N-(2-chlorobenzoyl)N'-[3,5-dichloro-4-(5-chloropyridyl-2-oxy)phenyl]urea | 100 | 60 |
| 16 | N-(2-chlorobenzoyl)N'-[4-(5-trifluoro-methylpyridyl-2-oxy)phenyl]urea | 100 | 80 |
| 17 | N-(2,6-difluorobenzoyl)N'-[3-chloro-4-(5-chloropyridyl-2-oxy)phenyl]urea | 100 | 100 |

EXPERIMENT 2

On radish young seedlings grown in unglazed pots, adults of diamondback moth were fed and kept for 24 hours to blow ova. One day later, aqueous dispersions of the active ingredients (500 ppm) were respectively sprayed on the young seedlings to fall drops of the dispersion and dried and kept in glass greenhouse. After 10 days from the treatment with the dispersion, the dead larvae were measured and the mortality rates were calculated by the equation $$\text{Mortality rate} = \frac{\text{dead larvae}}{\text{total hatched larvae}} \times 100.$$

The results are shown in Table 2.

Table 2

| NO. | Active ingredient | Mortality rate (%) |
|---|---|---|
| 1 | N-(2-chlorobenzoyl)N'-[3-chloro-4-(5-nitropyridyl-2-oxy)phenyl]urea | 80 |
| 2 | N-(2-chlorobenzoyl)N'-[3-chloro-4-(3,5-dibromopyridyl-2-oxy)phenyl]urea | 100 |
| 3 | N-(2-chlorobenzoyl)N'-[3-chloro-4-(3,5-dichloropyridyl-2-oxy)phenyl]urea | 100 |

EXPERIMENT 3

About 20 cc of germinated rice seeds were put into cups (diameter: 9 cm, height: 3 cm) to grow them. When they grew to seedlings having a height of 1 to 2 cm, the aqueous dispersions at specified concentrations were respectively sprayed at a ratio of 2 cc per 1 cup and dried, and larvae of rice stem borer (just hatched) were fed and the cups were covered. After 10 days from the treatment with the dispersion, the dead larvae were measured and the mortality rates were calculated by the equation of Experiment 1. The results are shown in Table 3.

Table 3

| No. | Active ingredient | Mortality rate (%) (concentration) 200 ppm | 100 ppm |
|---|---|---|---|
| 1 | N-(2-chlorobenzoyl)N'-[3-chloro-4-(5-bromopyridyl-2-oxy) phenyl] urea | 100 | 100 |
| 2 | N-(2-chlorobenzoyl)N'-[3-chloro-4-(5-nitropyridyl-2-oxy) phenyl] urea | 100 | 100 |
| 3 | N-(2-chlorobenzoyl)N'-[3-chloro-4-(3,5-dibromopyridyl)-2-oxy) phenyl] urea | 100 | 100 |
| 4 | N-(2-chlorobenzoyl)N'-[3-chloro-4-(3,5-dichloropyridyl-2-oxy) phenyl] urea | 100 | 100 |

EXPERIMENT 4

Young branches of persimmon tree cut in a length of 15 cm from the top, were respectively dipped into the aqueous dispersions of N-(2-chlorobenzoyl)N'-[3-chloro-4-(3,5-dichloropyridyl-2-oxy)phenyl]urea at various concentrations for 10 seconds, and they were dried and put into wide mouth bottles and larvae of gypsy moth in 2nd or 3rd instar were fed into them. The bottles were covered with gauze and kept in a constant temperature at 28° C. with lightening. After 7 days and 15 days from the treatment with the dispersion, the dead larvae were measured and the mortality rates and the abnormal rates were calculated. The results are shown in Table 4.

Table 4

| Observation | Mortality rate (%) (concentration) | | |
|---|---|---|---|
| | 400 ppm | 200 ppm | 100 ppm |
| After 7 days | 100 | 90 (10)* | 40 (30)* |
| After 15 days | 100 | 100 | 90 (10)* |

*abnormal rate

EXPERIMENT 5

N-(2-chlorobenzoyl)N'-[4-(3,5-dibromopyridyl-2-oxy)phenyl]urea was used to prepare the aqueous dispersions at specified concentrations. The effects of the dispersions to various insects were tested. The mortality rates after 10 days from the treatments were obtained in accordance with the process of Experiment 1.

The results are shown in Table 5.

Table 5

| Insects | Treatment | Concentration (ppm) | Mortality rate |
|---|---|---|---|
| cabbage armyworm: 2nd instar larvae (Lepidoptera) | cabbage leaf dipping | 50 | 100 |
| confused flour beetle: 2nd larval instar larvae (Coleoptera) | wheat flour blending | 200 | 100 |
| 1 sp. of sawfly 3rd instar larvae (Hymenoptera) | cherry branch spraying | 250 | 100 |

EXPERIMENT 6

200 ml of the aqueous dispersions at specified concentrations were respectively placed in glass containers with a capacity of 450 cc. 20 larvae of third instar of the mosquito (*Culex pipiens pallens*) were placed in each container and the containers were hold at 26°–28° C. with lightening. The mortality rates after 10 days from the treatments were obtained in accordance with the process of Experiment 1.

The results are shown in Table 6.

Table 6

| No. | Active ingredient | Mortality rate (%) | |
|---|---|---|---|
| | | 0.1 ppm | 0.01 ppm |
| 1 | N-(2-chlorobenzoyl)N'-[4-(3,5-dibromopyridyl-2-oxy)phenyl]urea | 100 | 100 |
| 2 | N-(2,6-difluorobenzoyl)N'-[4-(3,5-dichloropyridy-2-oxy)phenyl]urea | 100 | 100 |
| 3 | N-(2-chlorobenzoyl)N'-[4-(5-bromo-pyridyl)-2-oxy)phenyl]urea | 100 | 100 |

COMPOSITION 1

| (a) | N-(2-chlorobenzoyl)N'-[3-chloro-4-(3,5-dichloropyridyl-2-oxy)phenyl]urea | 20 wt. parts |
|---|---|---|
| (b) | Dimethyl sulfoxide | 70 wt. parts |
| (c) | Polyoxyethylenealkylphenyl ether | 10 wt. parts |

The components were uniformly blended to dissolve the ingredient to prepare an emulsifiable concentrate.

COMPOSITION 2

| (a) | N-(2-chlorobenzoyl)N'-[4-(3,5-dichloropyridyl-2-oxy)phenyl] urea | 5 wt. parts |
|---|---|---|
| (b) | Talc | 92 wt. parts |
| (c) | Sodium naphthalene sulfonate formaldehyde condensate | 3 wt. parts |

The mixture was pulverized to uniformly mix them to prepare dust.

COMPOSITION 3

| (a) | N-(2,6-dichlorobenzoyl)N'-[4-(3,5-dichloropyridyl-2-oxy phenyl]urea | 50 wt. parts |
|---|---|---|
| (b) | Jeeklite (fine divided clay) | 45 wt. parts |
| (d) | Sodium ligninsulfonate | 5 wt. parts |

The components were pulverized to uniformly mix them to prepare a wettable powder.

What is claimed is:

1. N-benzoyl N'-pyridyloxy phenyl urea having the formula

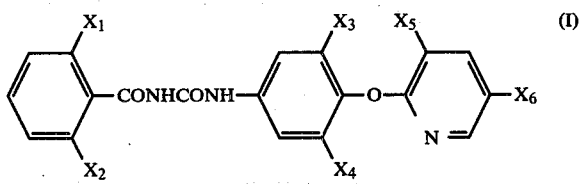

wherein $X_1$ represents a halogen atom; $X_2$ represents hydrogen or halogen atom; $X_3$ and $X_4$ respectively represent hydrogen or chlorine atom; $X_5$ represents hydrogen or halogen atom; $X_6$ represents a halogen atom or nitro or trifluoromethyl group.

2. N-benzoyl N'-pyridyloxy phenyl urea according to claim 1 which has the formula

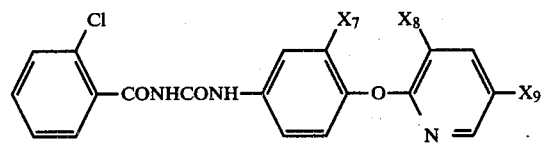

wherein $X_7$ represents hydrogen or chlorine atom and $X_8$ represents hydrogen or halogen atom; $X_9$ represents a halogen atom.

3. N-(2-chlorobenzoyl)N'-[4-(3,5-dibromopyridyl-2-oxy)phenyl]urea.

4. N-(2-chlorobenzoyl)N'-[4-(3,5-dichloropyridyl-2-oxy)phenyl]urea.

5. N-(2-chlorobenzoyl)N'-[3-chloro-4-(3,5-dichloropyridyl-2-oxy)phenyl]urea.

6. N-(2-chlorobenzoyl)N'-[3-chloro-4-(5-chloropyridyl-2-oxy)phenyl]urea.

7. N-benzoyl N'-pyridyloxy phenyl urea according to claim 1 which has the formula:

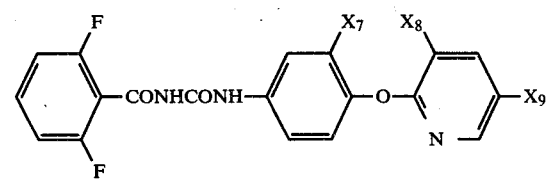

wherein $X_7$, $X_8$ and $X_9$ are defined in claim 2.

8. N-(2,6-difluorobenzoyl)N'-[4-(3,5-dichloropyridyl-2-oxy)phenyl]urea.

9. N-(2,6-difluorobenzoyl)N'-[3-chloro-4-(3,5-dichloropyridyl-2-oxy)phenyl]urea.

10. An insecticidal composition which comprises insecticidally effective amount N-benzoyl N'-pyridyloxy phenyl urea having the formula (I) according to claim 1 in admixture with a suitable carrier or adjuvant therefor.

11. An insecticidal composition according to claim 10 which comprises 0.5 to 80 wt. parts of N-benzoyl N'-pyridyloxy phenyl urea having the formula (I) and 20 to 99.5 wt. parts of an agricultural adjuvant.

12. An insecticidal composition according to claim 10 wherein the active ingredient is N-(2-chlorobenzoyl)N'-[4-(3,5-dibromopyridyl-2-oxy)phenyl]urea.

13. An insecticidal composition according to claim 10 wherein the active ingredient is N-(2-chlorobenzoyl)N'-[4-(3,5-dichloropyridyl-2-oxy)phenyl]urea.

14. An insecticidal composition according to claim 10 wherein the active ingredient is N-(2-[chlorobenzoyl)N'-chloro-4-(3,5-dichloropyridyl-2-oxy)phenyl]urea.

15. An insecticidal composition according to claim 10 wherein the active ingredient is N-(2-chlorobenzoyl)N'-[3-chloro-4-(5-chloropyridyl-2-oxy)phenyl]urea.

16. An insecticidal composition according to claim 10 wherein the active ingredient is N-(2,6-difluorobenzoyl)N'-[4-(3,5-dichloropyridyl-2-oxy)phenyl]urea.

17. An insecticidal composition according to claim 10 wherein the active ingredient is N-(2,6-difluorobenzoyl)N'-[3-chloro-4-(3,5-dichloropyridyl-2-oxy)phenyl]urea.

* * * * *